United States Patent [19]

Hutchison

[11] Patent Number: 4,871,465

[45] Date of Patent: Oct. 3, 1989

[54] CHLORINE-FREE SILVER PROTECTIVE LUBRICANT COMPOSITION (II)

[75] Inventor: David A. Hutchison, Naperville, Ill.

[73] Assignee: Amoco Corporation, Chicago, Ill.

[21] Appl. No.: 103,185

[22] Filed: Sep. 30, 1987

[51] Int. Cl.[4] ................. C10M 105/72; C10M 105/58
[52] U.S. Cl. ......................................... 252/47; 252/45
[58] Field of Search ................... 252/47, 47.5, 32.7 E, 252/391

[56] References Cited

U.S. PATENT DOCUMENTS

| | | | |
|---|---|---|---|
| 2,685,588 | 8/1954 | Goshorn | 252/47 |
| 2,690,999 | 10/1954 | Lowe | 252/47 |
| 2,765,289 | 10/1956 | Fields | 252/47 |
| 2,910,439 | 10/1959 | Fields | 252/47 |
| 3,338,832 | 8/1967 | LeSuer | 252/47.5 |
| 4,104,179 | 8/1978 | Colclough | 252/47 X |
| 4,136,043 | 1/1979 | Davis | 252/47.5 |
| 4,171,269 | 10/1979 | Sung et al. | 252/33 |
| 4,491,527 | 1/1985 | Lange et al. | 252/51.5 A |

Primary Examiner—William R. Dixon, Jr.
Assistant Examiner—James M. Hunter, Jr.
Attorney, Agent, or Firm—Matthew R. Hooper; William H. Magidson; Ralph C. Medhurst

[57] ABSTRACT

Silver protection in lubricant compositions is afforded by the combination of organo-sulfur compounds and hydrocarbon-substituted 1,2,4-triazoles, the latter being obtained by reaction of a substantially aliphatic, substantially saturated hydrocarbon-substituted dicarboxylic acid with an aminoguanidine compound. The invention is also directed to a method of silver protection utilizing the above combination.

18 Claims, No Drawings

CHLORINE-FREE SILVER PROTECTIVE LUBRICANT COMPOSITION (II)

BACKGROUND OF THE INVENTION

1. Field of the Invention

The present invention relates generally to lubricant compositions useful in medium speed diesel engines such as commonly found in railroad locomotives, marine towboats and stationary power applications. These engines frequently have silver bearings which necessitate lubricant compositions incorporating specialized silver protective agents to protect against wear, extreme pressure and corrosion of silver parts. However, it is well known that zinc-containing wear agents such as the zinc dihydrocarbyldithiophosphates (typically used in passenger cars) cannot be used for this purpose given their incompatibility with silver bearings. Although chlorine-containing wear agents have been used for silver protection, it is desirable to find alternatives to such chlorinated materials. Thus, the present invention, more particularly, is directed to a lubricating composition, preferably essentially free of zinc dihydrocarbyldithiophosphate compounds, and optionally free of chlorine-containing silver lubricity agents comprising a major proportion of an oil of lubricating viscosity and a minor amount of a silver protective agent comprising an organo-sulfur compound, preferably a thiadiazole compound having the general formula:

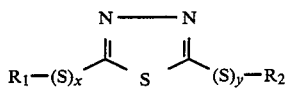

where x and y (the same or different) are integers from 1 to 5 and $R_1$ and $R_2$ (the same or different) are H or $C_1$ to $C_{50}$ hydrocarbyl in combination with the reaction product obtained by reacting a substantially aliphatic, substantially saturated hydrocarbon-substituted dicarboxylic acid wherein the hydrocarbon group contains at least about 20 aliphatic carbons, with (i) an aminoguanidine compound having the formula:

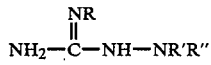

wherein R is H or $C_1$ to $C_{15}$ hydrocarbyl, and R' and R'' are H or $C_1$ to $C_{20}$ hydrocarbyl (R' and R'' being the same or different) or (ii) salts thereof, under reaction conditions giving rise predominantly to formation of a hydrocarbon-substituted 1,2,4-triazole.

The invention is further directed to a method for protecting silver parts in an internal combustion engine by lubricating the same with a lubricant composition comprising a major proportion of an oil of lubricating viscosity and a minor amount of the above-described combination. In accordance with the present invention, the combination results in a synergistic silver lubricity effect and obviates or markedly reduces the need for chlorine-containing silver lubricity agents.

2. Discussion of the Prior Art

Large numbers of medium speed diesel engines in the United States, as well as other countries, utilize silver-plated bearings, especially railway diesel engines. Thus, apart from providing stability against oxidation and protection against the formation of sludge and carbonaceous deposits, crankcase lubricating oils intended for use in medium speed diesel engines must also be formulated with specialized silver protecting agents in order that silver parts in the engine are not attacked either by the additives in the oil or by the dispersed neutralized decomposition products produced during extended engine operation. Such agents, often referred to as silver lubricity agents, protect against extreme pressure, wear and corrosion.

Although it is essential to include a silver lubricity agent in diesel oils intended for use in engines having silver parts, it is well known that such oils must exclude the zinc-containing anti-wear agents mentioned above, such as the zinc dihydrocarbyldithiophosphates, given the known propensity of the latter to damage the silver components of diesel engines. This is explained, for example, in U.S. Pat. No. 4,428,850 (column 1, lines 63-68).

The antagonism between zinc-containing wear inhibitors and the silver parts in diesel engines has been circumvented in the prior art by using alternative silver lubricity compounds, the most common of which are the chlorinated hydrocarbons such as shown in Sung, U.S. Pat. No. 4,171,269. However, while the chlorine compounds of the prior art have been shown to be effective in protecting the silver parts of diesel engines, the Occupational Safety and Health Administration in the United States and other public health agencies throughout the world have expressed concern over potential biological effects of chlorinated compounds. Therefore, an incentive exists to develop novel compositions effective in protecting the silver parts of medium speed diesel engines which overcome the problems or potential problems encountered with the zinc-containing and chlorine-containing wear inhibitors.

A number of patents are thought to be of relevance as background to the compositions and methods described in the present invention but do not address expressly, or even inherently, the problems described above. For example, Knepper et al., U.S. Pat. No. 4,595,523, is directed to a corrosion inhibiting composition comprising a triazole and an amine salt of an acid. While the patent states that "any amine which would form an acid salt which is soluble in an alcohol and inhibits corrosion may be used in the invention," there is no specific mention of carboxylic acid salts of aminoguanidine. Also, the invention of Knepper is clearly directed to a composition which is added to an alcohol fuel. Thus, the patent in no way relates to a lubricant composition, free of zinc compounds, which would be suitable for addition to a diesel engine lubricating composition used in a diesel engine having silver bearings.

Boehringer, et al., U.S. Pat. No. 3,749,702, describes metal deactivators useful as additives in lubricants and, more particularly, describes salts formed from amides prepared from benzoic acid or a substituted benzoic acid with aminoguanidine bicarbonate and an aliphatic or aromatic carboxylic acid. The present invention is not directed to the reaction product of a benzoic acid or its derivatives with aminoguanidine bicarbonate and is clearly distinguishable from Boeheringer, et al.

Lange, et al., U.S. Pat. No. 4,491,527, describes ester-heterocycle compositions useful as "lead paint" inhibitors in lubricants. In particular, at column 4, lines 34-51 (plus the accompanying drawings) the patentee describes the reaction of a substituted carboxylic acid (e.g., polybutylsuccinic acid) with an acyclic heterocycle precursor which cyclizes with the carboxylic acid group to form a heterocyclic compound. An illustrative acyclic heterocycle precursor which may react with an acid or an acid derivative group to form such heterocycles include aminoguanidine and salts thereof, semicarbazide, thiosemicarbazide, carbohydrazide and thiocarbohydrazide, as well as salts thereof such as aminoguanidine bicarbonate. Thus, the composition of Lange, et al. can include the 5-(polyalkenylsuccinic)-3-amino-1,2,4-triazole. The patent, however, is not specifically directed to a lubricant composition for use in diesel engines having silver parts. In fact, at column 12 of the patent, an illustrative lubricant composition of the invention is shown to include a zinc diaklylphosphorodithioate wear inhibitor which would be totally unacceptable in the present invention.

Sung, et al., U.S. Pat. No. 4,256,595, is directed to a diesel crankcase lubricant composition comprising a lubricating oil base and the reaction product of a hydrocarbyl succinic anhydride in which the hydrocarbyl radical has from 12 to 30 carbon atoms, and 5-aminotriazole. The background section of the patent states that it is known to employ a thiadiazole as a corrosion inhibitor for diesel crankcase lubricating oil. The patent, however, does not disclose or suggest a synergistic combination of hydrocarbon-substituted 3-amino-1,2,4-triazole compounds and 1,3,4-thiadiazole compounds, as disclosed in the present invention.

Davis, U.S. Pat. No. 4,136,043, is directed to compositions useful for suppression of copper activity and "lead paint" deposition and lubricants. The compositions are produced by preparing a mixture of an oil soluble dispersant (preferably a substantially neutral or acidic carboxylic dispersant) and a dimercaptothiadiazole, preferably 2,5-dimercapto-1,3,4-thiadiazole. As stated at column 4, lines 24–39, the carboxylic dispersants encompass nitrogen bridged dispersants wherein the nitrogen group is derived from aliphatic, aromatic, heterocyclic and carbocyclic amines as well as substituted ureas, thioureas, hydrozines, guanidines, amidines, amides, thioamides, cyanamides and the like. Davis is not directed to the achievement of silver lubricity in lubricating compositions for diesel engines.

In U.S. Pat. Nos. 3,272,746 and 3,341,542, Le Seur, et al., disclose lubricating oil compositions containing acylated nitrogen compounds prepared, for example, by reacting a substituted succinic acid or derivative thereof with a nitrogen-containing compound, such as ammonia, aliphatic amines, aromatic amines, heterocyclic amines, or carboxylic amines. The resulting detergent composition comprises an oil-soluble, acylated nitrogen composition characterized by the presence within its structure of (A) a substantially hydrocarbon-substituted polar group selected from the class consisting of acyl, acylimidoyl, and acyloxy radicals wherein the substantially hydrocarbon substituent contains at least about 50 aliphatic carbon atoms and (B) a nitrogen-containing group characterized by a nitrogen atom attached directly to said relatively polar group. In Example 38 of these patents, polyisobutene-substituted succinic anhydride, aminoguanidine bicarbonate, and mineral oil were mixed and heated at a temperature of 130° C. (266° F.) to 165° C. (329° F.) for 5 hours. The residue was mixed with mineral oil and heated to 150° C. (302° F.) and filtered. The resulting product was used as a lubricating oil additive and found to be an effective dispersant. These patents each that the mixture of acid-producing compound and the nitrogen-containing reactant is usually heated at a temperature above about 80° C. (176° F.), preferably, within the range of about 100° C. (212° F.) to about 250° C. (482° F.). These patents teach that guanidines are included in sources of nitrogen-containing compounds and present, as examples, guanidine, 1,3-diphenylguanidine, and 1,2,3-tributylguanidine. These patents do not indicate that the resulting product comprises triazoles. Furthermore, these patents do not disclose or suggest synergistic combinations of organo-sulfur compounds and hydrocarbon-substituted 1,2,4-triazoles.

SUMMARY OF THE INVENTION

In view of the problems cited earlier, a general object of the present invention is to provide a silver protective lubricant additive composition.

A further object of the invention is to provide a silver protective lubricant additive composition suitable for addition to lubricant compositions used to lubricate the moving parts of medium speed diesel engines such as found in railway locomotives, marine towboats and stationary power applications.

Another object of the invention is to provide a silver lubricity additive composition suitable for addition to lubricating compositions used to lubricate the moving parts of medium speed diesel engines, which additive composition provides enhanced protection against silver wear, corrosion and extreme pressure.

Still another object of the present invention is to provide a synergistic silver protective additive composition suitable for addition to lubricating compositions used in engines having silver parts, wherein the synergistic properties of such composition are evident from increased silver protection at reduced additive treat rates. Other objects appear hereinafter.

Yet another object of the present invention is to provide a silver protective lubricant composition which does not derive its silver lubricity characteristics from chlorinated silver lubricity agents.

We have now found that the foregoing objects are provided for in the present invention, namely, a lubricating composition essentially free of zinc-containing wear inhibitor compounds and comprising a major proportion of an oil of lubricating viscosity and a minor amount of a silver protective additive composition comprising an organo-sulfur compound, preferably a thiadiazole compound having the general formula:

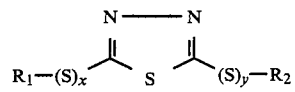

where x and y (being the same or different) are integers from 1 to 5 and $R_1$ and $R_2$ (being the same or different) are H or $C_1$ to $C_{50}$ hydrocarbyl and the product obtained by reacting a substantially aliphatic, substantially saturated hydrocarbon-substituted dicarboxylic acid wherein the hydrocarbon group contains at least about 20 aliphatic carbons, with a guanidine derivative having the formula:

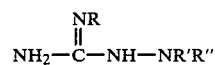

wherein $R_1$, is H or $C_1$, to $C_{15}$ aliphatic, $R_2$ is —NR'R" and R' and R" (the same or different) are H or $C_1$ to $C_{20}$ hydrocarbyl, under reaction conditions giving rise predominantly to formation of a hydrocarbon-substituted 1,2,4-triazole.

As a method, the invention is directed to the protection of silver engine parts in an internal combustion engine by lubrication thereof with the above-described lubricating composition.

A primary advantage in the synergistic silver protective agents prescribed for use in the lubricating compositions of the present invention, particularly in the context of medium speed diesel engines, is the fact that such agents are surprisingly effective substitutes for the chlorine-containing silver lubricity agents mentioned earlier which, heretofore, have been virtually a staple silver lubricity additive. The most frequently used chlorine-containing agents are the chlorinated paraffins exemplified by the commercial product "Chlorowax".

A further advantage of the present invention is an unexpected and pronounced synergistic effect observed in lubricating compositions according to the present invention which comprise the above-described inventive combination of an organo-sulfur compound, preferably a thiadiazole, and a triazole compound. The synergistic action of the present invention is evident in that the silver protection afforded by the organo-sulfur compound or the triazole, alone, can be significantly enhanced if these materials are used in combination in lubricant compositions as taught in the present invention. Such enhancement allows a lower treat rate of the synergistic combination needed to achieve a desired level of passing silver protection than would otherwise be required if either the thiadiazole or triazole were to be used alone.

DETAILED DESCRIPTION

The hydrocarbon-substituted triazole compound prescribed for use in the lubricating compositions of the present invention is the reaction product obtained upon reacting a substantially aliphatic, substantially saturated hydrocarbon-substituted carboxylic acid wherein the hydrocarbon group contains at least about 20 aliphatic carbons, with the aminoguanidine derivatives represented by the above formula under reaction conditions giving rise predominantly to formation of a hydrocarbon-substituted 1,2,4-triazole, preferably the 1,2,4-triazole-3-amine. Preferred aminoguanidine compounds useful in preparing the triazoles of the present invention are the salts of aminoguanidine wherein the anion is halide, carbonate, nitrate, phosphate, orthophosphate, citrate, fumarate, oxalate, etc. Particularly preferred is aminoguanidine bicarbonate.

The substantially saturated hydrocarbon-substituted carboxylic acid wherein the hydrocarbon group contains at least about 20 aliphatic carbons is preferably a high molecular weight alkyl-substituted dicarboxylic acid compound selected from the group consisting of alkyl-substituted dicarboxylic acids, alkyl-substituted dicarboxylic acid anhydrides, and mixtures thereof. Such substituted dicarboxylic acid compounds can be prepared by the alkylation of an unsaturated acid, an anhydride of such acid, or a mixture thereof, with homopolymers and interpolymers of polymerizable olefin monomers containing up to about 10 carbon atoms. Such polymers are produced typically from ethylene, propylene, 1-butene, 2-butene, isobutane, 1-hexene, or 1-octene and have at least about 15 carbon atoms in a chain. Also useful are copolymers of such olefins with other polymerizable olefinic substances, such as styrene, chloroprene, isoprene, para-methylstyrene and piperylene. In general, these copolymers should contain at least about 80 percent and preferably at least about 95 percent, on a weight basis, of units derived from the aliphatic mono-olefins. Olefin polymers having a number average molecular weight between about 300 and about 5,000 (as determined by gel permeation chromatography) are preferred, although higher polymers having higher molecular weights, for example, from about 10,000 to about 100,000 or higher, can also be used. Polybutene having a molecular weight of from about 850 to 2,500 is especially suitable as a hydrocarbon source.

The preferred acids contemplated for use in the present invention to make the desired hydrocarbon-substituted carboxylic acid compounds are unsaturated. Such acids and derivatives thereof as maleic acid, maleic anhydride, and fumaric acid and fumaric anhydride. Other possible dicarboxylic acid sources can be used however such as malonic acid, glutaric acid, adipic acid, and alkylated aromatic dicarboxylic acids, for example phthalic. A preferred acid and anhydride used to prepare the hydrocarbon-substituted dicarboxylic acid and/or anhydride is maleic acid or anhydride.

The substantially aliphatic, substantially saturated hydrocarbon-substituted dicarboxylic acid compound useful in preparing the triazole composition used in the present invention can be prepared by the reaction, according to well-known procedures, of a relatively low molecular weight dicarboxylic acid or derivative thereof with the hydrocarbyl-donating agent or hydrocarbon sources described earlier containing at least about 20 and preferably about 60 to 120 carbon atoms. The hydrocarbon source should be substantially aliphatic and should be substantially saturated. More specifically, preferably at least about 95 percent of the total number of carbon-to-carbon covalent linkages should be saturated. The hydrocarbon source is preferably substantially free from pendant groups containing more than about six aliphatic carbon atoms. The hydrocarbon source can be substituted, and examples of acceptable groups are halide, hydroxy, ether, keto, carboxyl, ester (especially lower carboxyalkoxy), amide, nitro, cyano, sulfoxide and sulfone. The substituents, if present, generally comprise no more than about 20 weight percent of the hydrocarbon source.

In many instances, the hydrocarbon source for use in preparing the carboxylic acid-producing compound should contain an activating polar group. This polar group can serve to facilitate reaction between the hydrocarbon source and a low-molecular weight dicarboxylic acid or derivative thereof when such a process is used to prepare the carboxylic acid-producing compound. Preferred polar groups are halogen, especially chlorine, but other suitable polar groups include sulfide, disulfide, nitro, mercapto, as well as ketone and aldehyde carbonyl groups.

Although any one of a number of known reactions can be employed for the preparation of the hydrocarbon substituted dicarboxylic acid, the reaction of an olefin polymer or a halogenated derivative thereof with maleic acid or maleic anhydride is particularly preferred for use in preparation of the hydrocarbon-substituted dicarboxylic acid. The resulting product is then the well-known hydrocarbyl-substituted succinic acid, or anhydride. The reaction involves merely heating the two reactants at a temperature from about 100° to about 250° C. Preferred is the polybutyl-succinic anhydride (PSA).

To prepare the triazole silver protective agent prescribed for use in the present invention, the above-mentioned PSA can be reacted with an aminoguanidine salt, preferably aminoguanidine bicarbonate, to obtain a reaction product which is highly effective as a silver protective agent in the lubricating compositions of the present invention. The desired reaction product can be obtained conveniently by reacting PSA and aminoguanidine bicarbonate in appropriate amounts at a temperature within the range of about 155° C. to about 200° C., preferably within the range of about 170° C. to about 190° C., and at atmospheric pressure. Of course, the reaction could be carried out at sub-atmospheric pressure or super-atmospheric pressure. In either case, the range of temperatures would be different from those listed for the reaction that is carried out at atmospheric pressure. A preferred ratio of reactants is about 1.6 moles of aminoguanidine bicarbonate per mole of PSA to about 2 moles of aminoguanidine bicarbonate per mole of PSA, preferably within the range of about 1.7 moles of aminoguanidine bicarbonate per mole of PSA to about 2 moles of aminoguanidine bicarbonate per mole of PSA. The reaction can be carried out for a period of time within the range of about one hour to about four hours, preferably within the range of about two hours to about four hours.

The resulting product is shown by spectral analysis to be principally a triazole. The reaction stoichiometry suggests primarily a bis-triazole having the following likely structure:

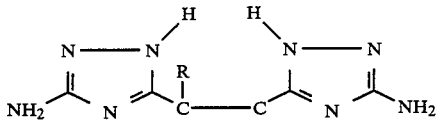

The product contains a relatively high nitrogen content, within the range of about 1.8 wt. % to about 2.9 wt. %. The five-membered ring of the triazole is considered to be aromatic. Depending upon the salt formed, the aminotriazole will exhibit both acidic and basic properties. The aminotriazoles are fairly stable to oxidizing agents and are extremely resistant to hydrolysis.

With no intention of being bound, it is proposed that the reaction of approximately 1 mole of PSA with 2 moles of aminoguanidine bicarbonate will initially result in the formation of a diamide, which can be seen in the infrared spectrum at the early stages of the reaction. In the presence of base, i.e., the carbonate, cyclization can occur easily to the five-membered triazol ring. During the cyclization water and carbon dioxide are evolved.

The lubricating compositions and methods of the present invention use synergistic combinations of the above triazole compounds and an organo-sulfur compound. While any organo-sulfur compound can be used in the present invention, preferred are compounds selected from the group consisting of sulfurized olefins, sulfurized fatty acids and esters, sulfur-containing heterocyclic compounds, sulfurized hydroxyaromatic compounds, disulfides, dithiocarbamates and thiadiazoles. Examples are 2-mercapto benzothiazole available from Vanderbilt under the trade name ROKON®, dibenzyl disulfide, 4,4,-methylene bid(dibutyldithio) carbamate available from Vanderbilt under the trade name Vanlube ® 7723. Particularly preferred are the 2,5-dimercapto-1,3,4 thiadiazole, the 2-mercapto-5-alkyldithio-1,3,4-thiadiazole, the 2,5-bis(alkyidithio)-1,3,4thiadiazole, and the 2-mercapto-5-alkylthio-1,3,4-thiadiazole. These compounds have the structural formulas shown below:

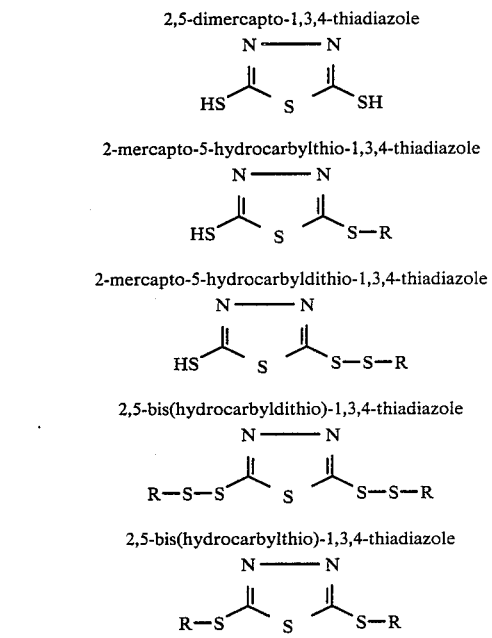

A particularly preferred 1,3,4-thiadiazole composition for use in the present invention is 2,5-bis (hydrocarbyldithio)-1,3,4-thiadiazole where the hydrocarbyl substituent of the thiadiazole is $C_1$ to $C_{30}$ alkyl. Most preferably, the hydrocarbyl is selected from the group consisting of heptyl, octyl, nonyl, decyl, undecyl, dodecyl, cetyl and isomers thereof.

The 1,3,4-thiadiazole compounds, or mixtures thereof, contemplated for use in the present invention can be readily obtained from commercial sources, such as the Amoco Petroleum Additives Company, or can be synthesized from hydrazine and carbon disulfide in a well-known manner. Particularly preferred for use in the invention are thiadiazole compositions commercially available from the Amoco Petroleum Additives Company under the trade names "Amoco-153" and "Amoco-158". U.S. Pat. Nos. 2,765,289; 2,749,311; 2,760,933; 2,850,453; 2,910,439; 3,663,561; 3,862,798; and 3,840,549 may be referred to for detailed procedures on the preparation of the 1,3,4-thiadiazole compounds contemplated for use in lubricating compositions of the present invention. These patents are incorporated by reference herein.

The lubricating compositions of the present invention comprise a major amount of an oil of lubricating viscosity and a minor amount of the silver protective synergistic combination of the present invention. The oil of lubricating viscosity suitable for use in preparing the lubricant compositions of the present inventions can be of synthetic, animal, vegetable or mineral origin. Ordinarily, mineral lubricating oils are used by reason of their availability, general excellence, and low cost. Normally, the lubricating oils preferred will be fluid oils, ranging in viscosity of about 40 Saybolt universal seconds at 100° Fahrenheit to about 200 Saybolt universal seconds at 210° Fahrenheit. The preferred lubricant oil for use in the compositions of the present invention is a mineral base oil. The mineral base oil can be a blend of lubricant oils having viscosities such that the final viscosity at 100° Centigrade of the lubricating oil composition is preferably in the range of about 12.0 to 17.0 CSt. Thus, the suitable base lubricant mineral oil is selected to conform to viscosity requirements. The mineral base oil used to prepare the lubricating composition of the present invention preferably comprises a major portion, i.e., at least about 70 percent, and still more preferably, at least about 85 percent, by weight of the total composition.

In addition to a major proportion of mineral oil of lubricating viscosity, the lubricating compositions of the present inventions contain a minor amount of the synergistic silver protective combination of an organo-sulfur compound, preferably a 1,3,4-thiadiazole compound and the 1,2,4-triazole compounds discussed above. A minor amount of the silver protective agents prescribed for use in the present invention which is sufficient to provide silver protection in the lubricating compositions of the present invention is an amount that is within the range of about 0.001 wt. % to about 10 wt. %, based on the weight of the lubricating oil composition. Preferably, the amount is within the range of about 0.1 wt. % to about 7 wt. % and, more preferably, the amount is within the range of about 0.2 wt. % to about 1.0 wt. %, based on the weight of the lubricating oil composition.

Generally speaking, in lubricant compositions of the present invention comprising the above-mentioned synergistic combination of the preferred 1,3,4-thiadiazole compounds and 1,2,4-triazole compounds, a lesser amount of such combination needs to be used to achieve an equivalent amount of silver protection than would otherwise be required if either the triazole or the thiadiazole compounds are used alone. For example, it has been found that passing silver scar performance can be obtained in a lubricant composition comprising as the sole silver protection agent a 1,3,4-thiadiazole composition at a treat rate of about 0.7 weight percent of the lubricant composition. The same lubricating composition fails silver scar performance where the sole silver protection agent is the triazole present at a treat rate of about 0.9 weight percent. Surprisingly, however, the same lubricating composition containing only 0.30 weight percent of the thiadiazole in combination with 0.60 weight percent of the oleyl aminotriazole shows dramatically improved silver scar performance, indicating a true synergy between the thiadiazole and the triazole as silver protection agents.

In addition to the organo-sulfur and triazole compounds, the lubricating compositions of the present invention can contain additional additives to impart qualities considered necessary in a lubricating oil such as dispersancy, detergency, oxidation inhibition foam inhibition, etc.

A class of oil-soluble dispersants suitable for incorporation in the lubricating compositions of the present invention are the Mannich dispersants obtained from the condensation under Mannich reaction conditions of a hydroxyaromatic compound, aldehyde-yielding reagent, and amine. Preferred Mannich reactants are: (a) a high molecular weight alkyl-substituted hydroxyaromatic whose alkyl substituent has a number average molecular weight of about 600–100,000, preferably a polyalkylphenol whose polyalkyl substituent is derived from 1-mono-olefin polymers (preferably polybutene) having an Mn of about 850–2,500; (b) an amine containing at least one primary or secondary —NH group, preferably an alkylene polyamine selected from the group consisting of diethylenetriamine, triethylenetetraamine, tetraethylenepentaamine, or mixtures thereof; and (c) an aldehyde, preferably formaldehyde, paraformaldehyde or formalin. The preparation of Mannich base dispersants (borated and non-borated) is disclosed in Piasek, et al., U.S. Pat. Nos. 3,697,574; 3,703,536; 3,704,308; 3,751,365; 3,756,953; 3,798,165; 3,798,247; and 3,803,039, all of which are incorporated herein by reference.

A further class of oil-soluble dispersants suitable for incorporation in the lubricating compositions of the present invention are the carboxylic polyamine dispersants, more frequently termed "succinimides," given that the most prevalently used dispersant in this class is the reaction product of an alkenyl-substituted succinic acid or anhydride with a nitrogen-containing compound. The succinic dispersants that can be used in the present invention are disclosed in numerous references and have become exceedingly well known in the art. Examples are taught in U.S. Pat. Nos. 3,172,892; 3,219,666; and 3,272,746. If desired, borated succinic dispersants can also be used. See for example, U.S. Pat. Nos. 3,087,936 and 3,254,025. A preferred succinic dispersant for use in the present invention is the reaction product of a polybutenyl succinic anhydride, wherein the polybutenyl group has a number average molecular weight between about 600 and 5,000, and the polyethylenepolyamine is selected from the group consisting of diethylenetriamine, triethylenetetraamine, tetraethylenepentaamine, and mixtures thereof.

A further class of dispersants suitable for use in the present invention is the succinate ester-amide dispersants, the latter term denoting the reaction product a long-chain aliphatic hydrocarbyl-substituted succinic acid or anhydride with an N-substituted hydroxyalkylamine. Representative patents disclosing this type of ashless dispersant are Malec, U.S. Pat. No. 4,426,305; and LeSeur, U.S. Pat. Nos. 3,219,666, 3,640,904 and 3,282,955, all of which are incorporated by reference. Preferred succinate ester-amide dispersants suitable for use in the lubricating compositions of the present invention are prepared by reacting a polybutenyl succinic acid composition and an alkylene diamine, preferably hexamethylenediamine, said alkylene diamine having an average of at least about 2.5 N-hydroxyalkyl groups. If desired, the succinate ester-amides can be borated with boron oxide, boron dihalides, boron acids, etc.

Another class of dispersants suitable for use in the present invention comprise the reaction products of aliphatic or alicyclic halides containing at least about 40 carbon atoms with amines, preferably, polyalkylene polyamines, examples of which dispersants are described in U.S. Pat. Nos. 3,275,554; 3,438,757; 3,454,555; and 3,565,804; all of which are incorporated by reference.

Still another type of dispersant which can be used in the lubricating compositions of the present inventions are polymers containing an oil-solubilizing group, for example a pendant alkyl group having at least about 8 carbon atoms, and a polar group, for example, interpolymers of decyl methacrylate, vinyl decyl ether, or a relatively high molecular weight olefin with aminoalkyl acrylates, aminoalkyl acrylamides, or poly-(oxyalkalene)-substituted alkyl acrylates, as well as copolymers of styrene, alkyl maleates, and maleic acid amides or imides respectively. Such polymers can generally be identified as polymeric polyamine dispersants and are exemplified in U.S. Pat. Nos. 3,329,658; 3,449,250; 3,519,565; 3,666,730; 3,687,849; and 3,702,300, all of which are incorporated herein by reference.

In addition to the dispersant compositions described above, the lubricating compositions of the present invention also preferably include basic detergent additives providing a TBN (total base number) of at least about 7, and preferably, within the range of about 10 to about 30. Examples of components that are suitable for providing the required TBN in the additive composition of the present invention are overbased alkali or alkaline earth metal sulfonates, phenates and salicylates. The sulfonates are normal or basic metal salts of petroleum sulfonic acids or long-chain alkyl-substituted benzene sulfonic acids. The phenates are normal or basic salts of alkylphenols, alkylphenol sulfides, and alkylphenol-aldehyde condensation products. As is known in the art, a normal metal salt of an acid is a salt which contains the stoichiometric amount of metal required for the neutralization of the acidic group or groups present in the acid, while a basic salt or overbased salt is a salt which contains more metal than is required to stoichiometrically neutralize the acidic group or groups present. While both normal and overbased sulfonates and phenates provide detergent properties for lubricating oil compositions, the preferred overbased or superbasic or hyperbasic salts provide unusually high detergent power and, consequently, have a much greater capacity to neutralize acidic contaminants than do the normal sulfonates and phenates. As is well known in the art, overbased sulfonate is prepared by mixing a promoter, catalyst or solvent with a normal sulfonate and a larger excess of metallic base, followed by heating, carbonation and filtration. Carbonation of the reaction mass, accomplished conveniently with carbon dioxide, is employed to increase the amount of metal base colloidally dispersed as metal carbonate in the filtered product. Phenols, trioacids of phosphorous, alcoholates, alcohols, ketones, and alkanolamines can be used as promoters for catalysts. Typical metallic bases are basic compounds of alkali or alkaline earth metals, such as sodium, calcium, barium or magnesium. Overbased metal sulfonates are discussed thoroughly in the prior art. Examples of such art are: U.S. Pat. Nos. 2,865,956; 2,956,018; 2,671,430; 3,779,920; 3,907,691; 4,137,184; 4,261,840; and 4,326,972. The overbased metal phenates are described in U.S. Pat. Nos. 2,680,096; 3,036,917; 3,178,368; 3,194,761; 3,437,595; 3,464,910; 3,779,920; and 4,518,807. All of the patents mentioned here are incorporated by reference. Numerous references also disclose methods of preparation for overbased salicylates.

A preferred lubricating composition embodying the present invention has a TBN of at least 5 and comprises: (1) a major amount of an oil of lubricating viscosity; (2) from about 0.05 to about 1.0 weight percent of the synergistic triazole/thiadiazole combination as set forth above; (3) from about 1 percent to about 10 weight percent of an ashless dispersant compound containing from about 40 weight percent to about 50 weight percent active component and selected from the group consisting of Mannich base dispersants, succinic dispersants, and succiate esteramide dispersants; (4) from about 0 to about 20 weight percent alkali or alkaline earth metal detergent compositions to provide alkalinity reserve, oxidation inhibition and detergency to the lubricating oil composition, said alkaline earth metal compositions being selected from the group consisting of calcium alkylsulfonates, magnesium alkylsulfonates, sodium alkylsulfonates, calcium alkylphenolates, magnesium alkylphenolates, calcium alkylsalicylates, magnesium alkylsalicylates, and mixtures thereof.

A particularly preferred embodiment of the present invention is a lubricant composition comprising (1) a major proportion of mineral oil of lubricating viscosity; (2) a Mannich dispersant comprising the reaction product of alkylphenol, a polyamine and formaldehyde; (3) an alkaline earth metal salt of a Mannich condensation reaction product comprising the reaction product of alkylphenol, formaldehyde and a polyamine; (4) an alkylbenzene sulfonate of an alkaline earth metal; (5) an overbased alkaline earth metal phenate; (6) the synergistic thiadiazole/triazole silver protecting combination; and (7) a small amount of a polydimethylsiloxane foam inhibitor.

The above embodiments can be prepared by suspending or dissolving in the mineral oil various additives. The mineral oil used can be selected to conform to viscosity requirements. Either a single base oil or blends of different viscosity base oils may be used as the base oil for the additive lubricant oil. The components may be blended in any order and in any combination. The first component of the preferred lubricant composition is the ashless dispersant, i.e., the Mannich condensation reaction obtained by reacting a polyalkylphenol, a polyamine and formaldehyde. The alkylphenol is commonly a high molecular weight alkyl-substituted hydroxyaromatic compound such as polypropyl phenol, polybutyl phenol or other alkylphenols. These alkylphenols may be obtained by the alkylation of phenol in the presence of an alkylating catalyst such as $BF_3$--HF, $BF_3$ or $AlCl_3$ with high molecular weight polypropene, polybutene or other polyalkene compounds to give alkyl substituents on the benzene ring of the phenol having a number average molecular weight of from about 600 to about 100,000. These alkyl-substituted hydroxyaromatic compounds may be derived from polypropenes, polybutenes and other polymers of monoolefins, principally 1-butene, 2-butene, isobutene and propene. Also, monomers may be copolymerized with propene or butene and other chlorinated, brominated or other derivatives of monoalkene compounds. The Mannich products may also contain fatty acids. The fatty acids compounds are thought to promote ease of production of the additives. The fatty acids also increase the detergency, the dispersancy and deposit preventing properties of the Mannich dispersants. Fatty acids such as oleic, linoleic, stearic and other $C_{16}$ to $C_{24}$ acids are suitable. Oleic acid is generally preferred. Preferably, the configuration of the alkyl-substituted hydroxyaromatic compound is that of para-alkylphenol. However, other alkylphenols are relatively reactive and thus useful in preparation of the Mannich dispersant. Representative amine reactants for use in preparing the Mannich dispersant preferred for use in the present invention are alkane polyamine, principally, polyethylene polyamines. Examples of polyamines which are useful are ethylamine, diethylamine, dimethylamine or propylamine; ethylenediamine, diethylenetriamine, triethylenetetraamine, tetraethylene pentaamine, pentaethylenehexamine, etc., and mixtures thereof. Representative aldehydes for use in preparing the Mannich dispersant include paraformaldehyde, formalin, acetaldehyde, and betahydroxybutyraldehyde.

Preferably a formaldehyde or formaldehyde-yielding reactant is used.

Component (3) prescribed for use in the preferred embodiment of the present invention is a low or high base alkylbenzene sulfonate. Such overbased alkylsulfonate is preferably produced from alkylated benzene sulfonic acid. The alkylated benzene sulfonic acid is generally produced by sulfonating benzene alkylates. The broad class of benzene alkylates include such compounds as polypropylbenzene, poly-1-butylbenzene, polyisobutylbenzene, poly-2-butylbenzene, polyethylenebenzene and copolymers of propyl and 1-butylbenzene and other various copolymers of ethylene, propene and butene isomers. The preferred alkylbenzenes are polypropyl, polybutyl and copolymer propyl butylbenzenes. Especially preferred are polypropylbenzenes wherein the alkyl moiety has a number average molecular weight of from about 400 to about 1,000. The alkaline metal salt which is used to overbase the alkylsulfonic acids may be chosen from a group consisting of barium oxide, calcium oxide, calcium hydroxide, magnesium oxide or other group 1 and 2 metal bases. Preferably, the overbased sulfonic acids are produced from calcium oxide. The alkylbenzenes are commonly sulfonated with fuming sulfuric acid or oleum, in standard industrial sulfonation procedures. The sulfonate is overbased when the sulfonate contains more base than is needed to neutralize the sulfonic acid. Degrees of overbasing are measured in the form of total base number by ASTM D-2896. Total base number is equivalent to the milligrams of KOH equivalent to the amount of base in the composition which exceeds the amount needed to neutralize the sulfonic acids. TBN's of 1-400 are common.

Component (4) prescribed for use in the preferred embodiment of the present invention is the alkaline earth salt of an alkylphenol, formaldehyde, polyamine Mannich reaction product, preferably the calcium Mannich phenate. Phenols which have utility in this application are the alkylated phenols such as methyl, ethyl, propyl, butyl, pentyl, hexyl, heptyl, octyl, nonyl, decyl, undecyl, dodecyl, phenyl and the like. Also useful are alkylated phenols such as polyalkyl phenols formed from polyalkylenes and phenols. Formaldehyde may be in the form of paraformaldehyde formalin or other well-known formaldehyde reactants. Polyamines such as ethylenediamine, diethylenetriamine, and tetraethylenepentaamine find utility in preparation of the calcium Mannich phenate. The Mannich condensation reaction product is overbased using an alkaline earth metal salt containing calcium, barium or magnesium to obtain a TBN of from about 1 to about 170. The metal may be in the form of oxides or hydroxides or carbonates. The preferred alkaline earth metal is calcium.

Component (5) prescribed for use in the preferred embodiment of the present invention is an overbased alkaline earth metal sulfurized alkylphenate sulfide used as an alkalinity agent/detergent. Alkylphenols such as decyl, nonyl, octyl or other phenols can be alkylated using polyalkylenes in a well-known manner. The alkylphenols react with an alkali or alkaline earth metal such as sodium, calcium or magnesium to form a metal salt of an alkylphenate. Preparation of a sulfurized alkylphenol using elemental sulfur can be carried out using conventional techniques. TBN's from about 1 to about 300 may be obtained. A preferred alkaline earth metal salt of a sulfurized alkylphenate in the present invention is the high base sulfurized calcium phenate detergent available from the Amoco Petroleum Additives Company under the trade name "Amoco-9213".

Component (6) for use in the preferred embodiment of the present invention comprises the silver protective synergistic combination as described in detail earlier.

Finally, Component (7) is preferably a silicon antifoam agent commonly used in the art and generally identified as a polydimethylsiloxane. The typically properties at 77° F. are viscosity in the range of about 10 to about 100,000 centistokes, pour point of about 40° F. to about 60° F., specific gravity of about 0.900 to about 0.995.

While it has been stated that additional additive agents may be incorporated in the lubricating compositions of the present invention, it is important that the lubricant composition of the present invention exclude zinccontaining wear agents if the lubricating compositions are used in diesel engines containing silver parts. This exclusion is intended to exclude amounts of zinc-containing wear inhibitors such as the zinc dihydrocarbyl dithiophosphate compounds sufficient to exert a measurable deleterious effect upon silver parts. At lesser amounts having no measurable effect, the lubricant is considered essentially free of zinc compounds for purposes of the present invention. If used in other engine environments which do not contain silver parts, the additives of the present invention can provide useful lubricity, wear, and anti-corrosion properties and may be used in conjunction with zinc compounds.

Insofar as the present invention provides effective substitutes for chlorine-containing silver lubricity agents, such as chlorinated paraffins, a preferred embodiment of the present invention is one which excludes such agents.

The present invention is further illustrated by the following examples which are not, however, to be construed as limitations thereof.

EXAMPLE I

Preparation of Polybutenyl Bis-1H-1,2,4-triazol-3-Amine

Into a three-liter, three-necked, round bottom flask under nitrogen is charged 1000 grams of a polybutenyl succinic anhydride (PSA) in oil solution (0.25 moles PSA; 57.5% activity) obtained by reacting maleic anhydride with polybutene having a molecular weight of about 2060; 69.9 g of 98.5% aminoguanidine bicarbonate (0.50 mole); and 494 g of a 100 neutral base oil. The mixture was heated, with constant stirring, for three hours at a temperature of 100° C. to form polybutenyl bis-3-amino-1,2,4-triazole. The product (40% active) was filtered before use.

EXAMPLE II

Example I was repeated, except that polybutene having a number average molecular weight of about 1300 was used to prepare the PSA.

EXAMPLE III

Example I was repeated, except that polybutene having a number average molecular weight of about 950 was used to prepare the PSA.

EXAMPLE IV

This Example illustrates the synergism between thiadiazole compounds, in particular 2,5-bis-(dinonylthio)-1,3,4-thiadiazole and the polybutenyl base 1,2,4-triazol- 3-amine of Example I. This synergism was examined in the following formulation:

| Component | Wt. % |
|---|---|
| Mannich Dispersant | 3.3 |
| Calcium Mannich Phenate | 4.8 |
| Calcium Sulfonate | 2.0 |
| Calcium Sulfurized Phenate | 1.65 |
| SX-5 | 0.2 |
| Silver Lubricity Agent | .1 to .9 |

| Blend | Wt. % Thiadiazole | Wt. % Triazole | Silver Scar (Pass = <1.9) |
|---|---|---|---|
| 1 | 0.00 | 0.5 | 3.27 |
| 2 | 0.00 | 0.70 | 3.09 |
| 3 | 0.00 | 0.90 | 3.06 |
| 4 | 0.50 | 0.0 | 1.62 |
| 5 | 0.70 | 0.0 | 1.68 |
| 6 | 0.90 | 0.0 | 1.78 |
| 7 | 0.10 | 0.40 | 2.22 |
| 8 | 0.15 | 0.40 | 2.17 |
| 9 | 0.20 | 0.40 | 1.99 |
| 10 | 0.30 | 0.40 | 1.47 |
| 11 | 0.15 | 0.45 | 1.94 |
| 12 | 0.20 | 0.45 | 1.60 |
| 13 | 0.25 | 0.45 | 1.60 |
| 14 | 0.10 | 0.50 | 2.22 |
| 15 | 0.15 | 0.50 | 2.02 |
| 16 | 0.20 | 0.50 | 1.57 |
| 17 | 0.25 | 0.50 | 1.43 |
| 18 | 0.30 | 0.50 | 1.38 |
| 19 | 0.15 | 0.55 | 1.80 |
| 20 | 0.20 | 0.55 | 1.60 |
| 21 | 0.25 | 0.55 | 1.54 |
| 22 | 0.30 | 0.55 | 1.56 |
| 23 | 0.10 | 0.60 | 2.22 |
| 24 | 0.15 | 0.60 | 1.96 |
| 25 | 0.20 | 0.60 | 1.74 |
| 26 | 0.25 | 0.60 | 1.54 |
| 27 | 0.30 | 0.60 | 1.31 |

EXAMPLE V

Blend 27 from the preceding Example was diesel engine-tested in the EMD 2-567C test of medium-speed diesel engine oils.

The lubricant base oil was a combination of 16.35 wt. % Amoco "SX-20", 29.60 wt. % Amoco "HX-40", and 41.20 wt. % Exxon "HP-1200". The results were as follows:

| Silver Wear | 1.26 |
|---|---|
| Bearing Right | 6.0 |
| Bearing Left | 15.0 |
| Average Distress | 10.5 | passing is Avg. Distress <40

We claim:

1. A lubricating composition for use in railway diesel engine which is essentially free of zinc dialkydithiophosphate wear inhibitors and which comprises a major proportion of an oil of lubricating viscosity and a minor effective amount of a silver protective additive comprising the combination of (I) an organo sulfur compound selected from the group consisting of sulfurized olefins, sulfurized fatty acids, sulfurized hydroxyaromatics, 1,3,4-thiadiazoles, and dithiocarbamates; and (II) the reaction product obtained by reacting polybutyl-succinic anhydride in which the polybutyl group has a number average molecular weight of from about 300 to about 5000 with (a) an aminoguanidine compound having the formula:

wherein R is H or $C_1$ to $C_{15}$ hydrocarbyl and wherein R' and R" being the same or different are H or $C_1$ to $C_{20}$ hydrocarbyl;

or (b) salts of said aminoguanidine compound, under reaction conditions giving rise predominantly to formation of a polybutenyl-substituted 1,2,4-triazole.

2. A lubricating composition for use in railway diesel engines containing silver parts which is essentially free of zinc dialkyldithiophosphate wear inhibitors and which comprise a major proportion of an oil of lubricating viscosity and a minor effective amount of a silver protective additive comprising the combination of (I) a thiadiazole compound having the general formula:

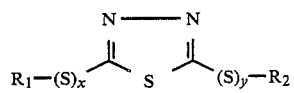

wherein x and y, being the same or different, are integers from 1 to 5 and $R_1$ and $R_2$, being the same or different, are H or $C_1$ to $C_{50}$ hydrocarbyl; and (III) the reaction product obtained by reacting polybutyl-succinic anhydride in which the polybutyl group has a number average molecular weight of from about 300 to about 5000 with (a) an aminoguanidine compound having the formula:

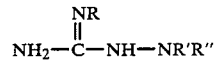

wherein R is H or $C_1$ to $C_{15}$ hydrocarbyl and wherein R' and R" being the same or different are H or $C_1$ to $C_{20}$ hydrocarbyl;

or (b) salts of said aminoguanidine compound, under reaction conditions giving rise predominantly to formation of a polybutyl-substituted 1,2,4,-triazole.

3. The lubricating composition of claim 2 wherein reaction product (II) is obtained by reacting an inorganic salt of said aminoguanidine compound where R is H with said polybutyl-succinic anhydride, in a mole ratio, respectively, of from about 1.6:1 to about 2:1, at a temperature within the range of from about 155° C. to about 200° C. to obtain a product that comprises predominantly a polybutyl-substituted bis-3-amino-1,2,4-triazole.

4. The lubricating composition of claim 3 wherein R' and R" are H; and the aminoguanidine salt is aminoguanidine bicarbonate.

5. The lubricating composition of claim 3 wherein the thiadiazole is at least one member selected from the group consisting of 2,5-dimercapto-1,3,4-thiadiazole; 2-mercapto-5-hydrocarbyldithio-1,3,4-thiadiazole; 2,5-bis(hydrocarbyldthio)-1,3,4-thiadiazole; and 2-mercapto-5-hydrocarbylthio-1,3,4-thiadiazole where the hydrocarbyl group is $C_1$ to $C_{20}$ alkyl.

6. The lubricating composition of claim 5 wherein the thiadiazole is 2,5-bis(nonyldithio)-1,3,4-thiadiazole.

7. The lubricant composition of claim 5 further comprising an ashless dispersant selected from the group consisting of Mannich, succinimide, and succinate ester-amide dispersants.

8. The lubricant composition of claim 7 comprising an overbased alkali or alkaline earth metal sulfonate, phenate or salicylate.

9. The lubricating composition of claim 8 comprising a Mannich dispersant, an alkaline earth metal Mannich phenate, an overbased magnesium or calcium sulfonate, and an overbased calcium sulfurized phenate.

10. A method for protecting silver engine parts in an internal combustion engine comprising the step of contacting the internal portion of said engine with a lubricating composition essentially free of zinc dialkyldithiophosphate wear inhibitors and comprising a major proportion of an oil of lubricating viscosity and a minor effective amount of a silver protective additive composition comprising the combination of (I) a thiadiazole compound having the general formula:

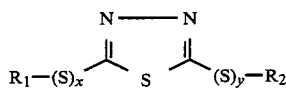

wherein x and y, being the same or different, are integers from 1 to 5 and $R_1$ and $R_2$, being the same or different, rre H, or $C_1$ to $C_{50}$ hydrocarbyl; and (II) the reaction product obtained by reacting a substantially aliphatic, substantially saturated hydrocarbon substituted dicarboxylic and wherein the hydrocarbon group contains at least about 20 aliphatic carbons, with (a) an aminoguanidine compound having the formula:

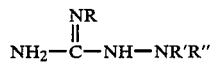

wherein R is H or $C_1$ to $C_{15}$ hydrocarbyl and wherein R' and R" being the same or different are H or $C_1$ to $C_{20}$ hydrocarbyl;

or (b) salts of said aminoguanidine compound, under reaction conditions giving rise predominantly to formation of a hydrocarbon-substituted 1,2,4-triazole.

11. The method of claim 10 wherein reaction product (II) is obtained by reacting an inorganic salt of said aminoguanidine compound where R is H with a substantially aliphatic, substantially saturated hydrocarbon-substituted dicarboxylic acid or anhydride in a mole ratio, respectively, of from about 1.6:1 to about 2:1, at a temperature within the range of from about 170° C. to about 190° C. to obtain a product that comprises predominantly a hydrocarbon-substituted bis-3-amino-1,2,4-triazole.

12. The method of claim 11 wherein R' and R" are H; the substantially aliphatic, substantially saturated hydrocarbon-substituted dicarboxylic acid or anhydride is polybutenyl succinic anhydride, a polybutenyl succinic acid, or a mixture thereof, and the aminoguanidine salt is aminoguanidine bcarbonate.

13. The method of claim 12 wherein the hydrocarbon substituted dicarboxylic acid or anhydride is polybutenyl succinic anhydride having a number average molecular weight of from about 850 to about 2500.

14. The method of claim 11 wherein the thiadiazole is at least one member selected from the group consisting of 2,5-dimercapto-1,3,4-thiadiazole; 2-mercapto-5-hydrocarbyldithio-1,3,4-thiadiazole; 2,5-bis(hydrocarbyldithio)-1,3,4-thiadiazole; and 2-mercapto-5-hydrocarbylthio-1,3,4-thiadiazole where the hydrocarbyl group is $C_1$ to $C_{20}$ alkyl.

15. The method of claim 14 wherein the thiadiazole is 2,5-bis(nonyldithio)-1,3,4-thiadiazole.

16. The method of claim 14 further comprising an ashless dispersant selected from the group consisting of Mannich, succinimide, and succinate, ester-amide dispersants.

17. The method of claim 16 comprising an overbased alkali or alkaline earth metal sulfonate, phenate or salicylate.

18. The method of claim 17 comprising a Mannich dispersant, an alkaline earth metal Mannich phenate, an over-based magnesium or calcium sulfonate, and an overbased calcium sulfurized phenate.

* * * * *